United States Patent
Gonzalez et al.

(10) Patent No.: US 9,034,338 B2
(45) Date of Patent: May 19, 2015

(54) NUCLEIC ACID AND AMINO ACID SEQUENCES, AND VACCINE FOR THE CONTROL OF ECTOPARASITE INFESTATIONS IN FISH

(75) Inventors: Yamila Carpio Gonzalez, Habana (CU); Mario Pablo Estrada Garcia, Habana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 1193 days.

(21) Appl. No.: 12/601,974

(22) PCT Filed: May 30, 2008

(86) PCT No.: PCT/CU2008/000003
§ 371 (c)(1),
(2), (4) Date: May 11, 2010

(87) PCT Pub. No.: WO2008/145074
PCT Pub. Date: Dec. 4, 2008

(65) Prior Publication Data
US 2010/0221271 A1 Sep. 2, 2010

(30) Foreign Application Priority Data
May 31, 2007 (CU) .................................. 2007-0124

(51) Int. Cl.
| | | |
|---|---|---|
| *A61K 39/395* | (2006.01) | |
| *A61K 39/00* | (2006.01) | |
| *A61K 39/38* | (2006.01) | |
| *C07K 1/00* | (2006.01) | |
| *C07K 14/00* | (2006.01) | |
| *C07K 17/00* | (2006.01) | |
| *C07H 21/02* | (2006.01) | |
| *C07H 21/04* | (2006.01) | |
| *C07K 14/435* | (2006.01) | |
| *A23K 1/18* | (2006.01) | |
| *A61K 38/00* | (2006.01) | |

(52) U.S. Cl.
CPC ..... *C07K 14/43509* (2013.01); *A61K 2039/552* (2013.01); *A23K 1/188* (2013.01); *A61K 38/00* (2013.01); *A61K 39/00* (2013.01); *A61K 2039/53* (2013.01); *C07K 2319/00* (2013.01)

(58) Field of Classification Search
CPC . A23K 1/188; A61K 2039/552; A61K 38/00; C07K 2319/00
See application file for complete search history.

(56) References Cited

U.S. PATENT DOCUMENTS

2006/0234905 A1   10/2006   Estrada Garcia et al.

FOREIGN PATENT DOCUMENTS

| WO | WO2006010265 A1 | 2/2006 |
|---|---|---|
| WO | WO2006127322 A2 | 11/2006 |
| WO | WO2007039599 A1 | 4/2007 |

OTHER PUBLICATIONS

Bowie et al. (Science, 1990, 257: 1306-1310).*
Brooks, Journal of Fish Diseases, 2009; 32(1): 59-73.*
Jaillion et al., "Description and Origin of the Protein" Full=chromosome 14 SCAF15003, whole genome shotgun sequence, Database UniProt XP-002504096, pp. 1-3 (2005).
Jallion et al., "Genome Duplication in the Teleost Fish *Tetraodon nigtroviridis* Reveals the Early Vertebrate Proto-Karyotype", Nature, vol. 431, pp. 946-957 (2004).
Raynard et al., "Development of Vaccines Against Sea Lice", Society of Chemical Industry, Pest Management Science, pp. 569-575 (2002), vol. 58.
Almazan et al., "Characterization of Three *Ixodes scapularis* cDNAs Protective Against Tick Infestations", Vaccine, 23 No. 35, pp. 4403-4416 (2005).
de la Fuente et al., "RNA Interference Screening in Ticks for Identification of Protective Antigens", Parasitology Research, vol. 96, pp. 137-141 (2005).
Labus et al., "Identification and Expression of Antigens from *Lepeophtheirus salmonis* for Use in Vaccination Trials", Biochemical Society Transactions, vol. 24, No. 2, p. 254S (1995).
Kvamme et al., "The Cloning and Characterisation of Full-Length Trypsins from the Salmon Louse *Lepeophtheirus salomis*", Molecular and Biochemical Parasitology, vol. 136, pp. 303-307 (2004).
Raynard et al., "Development of a Vaccine for the Control of Sea Lice (*Lepeophtheirus salmonis* and *Caligue elonatus*) in Atlantic Salmon" Ices Council Meeting Papers, vol. 22, No. 30, pp. 1-6 (1994).
Gonzalez et al., "Life Cycle of *Caligus rogercresseyi*, (Copepoda: Caligidae) Parasite of Chilean Reared Salmonids", Aquaculture, vol. 220, No. 1-4, pp. 101-117 (2003).

\* cited by examiner

*Primary Examiner* — Gary Nickol
*Assistant Examiner* — Lakia Tongue
(74) *Attorney, Agent, or Firm* — Hoffmann & Baron, LLP

(57) ABSTRACT

The present invention is related with the isolation and cloning of a new gene, the production of the protein encoded by this gene by using recombinant systems, and the use of this antigen in a vaccine formulation as a purified protein and/or naked DNA, to induce an immune response in aquatic organisms against different ectoparasite species, including the known as sea lice, and pathogens associated with these infestations. The vaccine preparations, administered by oral route, immersion bath or injection, demonstrated its efficacy by producing IgM humoral immune response and reducing the number of parasites per fish in the vaccinated fishes.

13 Claims, 2 Drawing Sheets

SEQUENCE LISTING

<160> NUMBER OF SEQ ID NOS: 10

<210> SEQ ID NO 1
<211> LENGTH: 581
<212> TYPE: DNA
<213> ORGANISM: Artificial Sequence
<220> FEATURE:
<223> OTHER INFORMATION: Synthetic DNA sequence obtained by Reverse
      Transcription-Polymerase chain reaction from total RNA of
      synthetic rogercresseyi

<400> SEQUENCE: 1

```
atggcttgcg cgacgttgaa gcgtcccttg gactttgacc ccttcactc ccccaaccgt    60 cctcctaaca agcgtcagcg gcgatgcctt cccctcgcac gacagtccct ggagacgtcc   120
tcctctctca tggcttcacc aacacattca caaagggact ccgtgttccg tgagtctcct   180
ttgtcagccg gagagatcgc cgtgaatctt cgtgatgagc tcaagcgcct caagcgtcgt   240
cgtgccctcg cggggcagcc agagagtccc ccgttgtgca gccagagcag catgggggac   300
tcgcttggga gcccacaggg aaacagcggc tcctccggaa cattggctgc tgctactgct   360
gcttgtcgaa gcccttcaca cgcatcttcc tcctcccccg ccggcacaac cggatcatcc   420
tcctcttcaa gcgccaacaa cagagaaaaa cccactttca cgctcaagca aatgacgctc   480
atttgtgaac ggatgtgcaa ggaacgcacg gatcaagttc gggaggagta cgataagatc   540
ctccatcaaa agctaacgga acaatacgac gcctttgtta a                      581
```

<210> SEQ ID NO 2
<211> LENGTH: 194
<212> TYPE: PRT
<213> ORGANISM: Artificial Sequence
<220> FEATURE:
<223> OTHER INFORMATION: Synthetic polypeptide amino acid sequence
      deduced from the DNA complementary sequence synthetic from Caligus
      rogercresseyi

<400> SEQUENCE: 2

```
Met Ala Cys Ala Thr Leu Lys Arg Pro Leu Asp Phe Asp Pro Leu His
1               5                   10                  15

Ser Pro Asn Arg Pro Asn Lys Arg Gln Arg Arg Cys Leu Pro Leu
            20                  25                  30

Ala Arg Gln Ser Leu Glu Thr Ser Ser Ser Leu Met Ala Ser Pro Thr
        35                  40                  45

His Ser Gln Arg Asp Ser Val Phe Arg Glu Ser Pro Leu Ser Ala Gly
    50                  55                  60

Glu Ile Ala Val Asn Leu Arg Asp Glu Leu Lys Arg Leu Lys Arg Arg
65                  70                  75                  80

Arg Ala Leu Ala Gly Gln Pro Glu Ser Pro Pro Leu Cys Ser Gln Ser
                85                  90                  95

Ser Met Gly Asp Ser Leu Gly Ser Pro Gln Gly Asn Ser Gly Ser Ser
            100                 105                 110

Gly Thr Leu Ala Ala Ala Thr Ala Ala Cys Arg Ser Pro Ser His Ala
        115                 120                 125

Ser Ser Ser Ser Pro Ala Gly Thr Thr Gly Ser Ser Ser Ser Ser
    130                 135                 140

Ala Asn Asn Arg Glu Lys Pro Thr Phe Thr Leu Lys Gln Met Thr Leu
145                 150                 155                 160

Ile Cys Glu Arg Met Cys Lys Glu Arg Thr Asp Gln Val Arg Glu Glu
                165                 170                 175
```

Tyr Asp Lys Ile Leu His Gln Lys Leu Thr Glu Gln Tyr Asp Ala Phe
        180                 185                 190

Val Lys

<210> SEQ ID NO 3
<211> LENGTH: 21
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(6)
<223> OTHER INFORMATION: n = T or C
<220> FEATURE:
<221> NAME/KEY: misc_feature
<222> LOCATION: (9)..(9)
<223> OTHER INFORMATION: n = T or C
<220> FEATURE:
<221> NAME/KEY: misc_feature
<222> LOCATION: (12)..(12)
<223> OTHER INFORMATION: n = T,C,G or A
<220> FEATURE:
<221> NAME/KEY: misc_feature
<222> LOCATION: (15)..(15)
<223> OTHER INFORMATION: n = T,C,G or A
<220> FEATURE:
<221> NAME/KEY: misc_feature
<222> LOCATION: (16)..(16)
<223> OTHER INFORMATION: n = T or C
<220> FEATURE:
<221> NAME/KEY: misc_feature
<222> LOCATION: (18)..(18)
<223> OTHER INFORMATION: n = T or C
<220> FEATURE:
<221> NAME/KEY: misc_feature
<222> LOCATION: (21)..(21)
<223> OTHER INFORMATION: n = A or G

<400> SEQUENCE: 3
atggcntgng cacnntnaa n                                            21

<210> SEQ ID NO 4
<211> LENGTH: 21
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(6)
<223> OTHER INFORMATION: n = T or C
<220> FEATURE:
<221> NAME/KEY: misc_feature
<222> LOCATION: (9)..(9)
<223> OTHER INFORMATION: n = T or C
<220> FEATURE:
<221> NAME/KEY: misc_feature
<222> LOCATION: (12)..(12)
<223> OTHER INFORMATION: n = T, C, G or A
<220> FEATURE:
<221> NAME/KEY: misc_feature
<222> LOCATION: (15)..(15)
<223> OTHER INFORMATION: n = T, C, A or G
<220> FEATURE:
<221> NAME/KEY: misc_feature
<222> LOCATION: (16)..(16)
<223> OTHER INFORMATION: n = T or C
<220> FEATURE:
<221> NAME/KEY: misc_feature
<222> LOCATION: (18)..(18)
<223> OTHER INFORMATION: n = A or G
<220> FEATURE:
<221> NAME/KEY: misc_feature
<222> LOCATION: (21)..(21)

```
<223> OTHER INFORMATION: n = A or G

<400> SEQUENCE: 4
atggcntgng cnacnntnaa n                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(6)
<223> OTHER INFORMATION: n = G or A
<220> FEATURE:
<221> NAME/KEY: misc_feature
<222> LOCATION: (9)..(9)
<223> OTHER INFORMATION: n = T or C
<220> FEATURE:
<221> NAME/KEY: misc_feature
<222> LOCATION: (12)..(12)
<223> OTHER INFORMATION: n = T, C, G or A
<220> FEATURE:
<221> NAME/KEY: misc_feature
<222> LOCATION: (15)..(15)
<223> OTHER INFORMATION: n = T, C, A or G
<220> FEATURE:
<221> NAME/KEY: misc_feature
<222> LOCATION: (16)..(16)
<223> OTHER INFORMATION: n = T or C
<220> FEATURE:
<221> NAME/KEY: misc_feature
<222> LOCATION: (18)..(18)
<223> OTHER INFORMATION: n = T or C
<220> FEATURE:
<221> NAME/KEY: misc_feature
<222> LOCATION: (21)..(21)
<223> OTHER INFORMATION: n = A or G

<400> SEQUENCE: 5
atggcntgng cnacnntnaa n                                              21

<210> SEQ ID NO 6
<211> LENGTH: 21
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(6)
<223> OTHER INFORMATION: n = G or A
<220> FEATURE:
<221> NAME/KEY: misc_feature
<222> LOCATION: (9)..(9)
<223> OTHER INFORMATION: n = T or C
<220> FEATURE:
<221> NAME/KEY: misc_feature
<222> LOCATION: (12)..(12)
<223> OTHER INFORMATION: n = T, C, G or A
<220> FEATURE:
<221> NAME/KEY: misc_feature
<222> LOCATION: (15)..(15)
<223> OTHER INFORMATION: n = T, C, A or G
<220> FEATURE:
<221> NAME/KEY: misc_feature
<222> LOCATION: (16)..(16)
<223> OTHER INFORMATION: n = T or C
<220> FEATURE:
<221> NAME/KEY: misc_feature
<222> LOCATION: (18)..(18)
<223> OTHER INFORMATION: n = A or G
<220> FEATURE:
<221> NAME/KEY: misc_feature
```

-continued

```
<222> LOCATION: (21)..(21)
<223> OTHER INFORMATION: n = A or G

<400> SEQUENCE: 6
atggcntgng cnacnntnaa n                                              21

<210> SEQ ID NO 7
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (3)..(3)
<223> OTHER INFORMATION: n = A or C
<220> FEATURE:
<221> NAME/KEY: misc_feature
<222> LOCATION: (6)..(6)
<223> OTHER INFORMATION: n = A or G
<220> FEATURE:
<221> NAME/KEY: misc_feature
<222> LOCATION: (9)..(9)
<223> OTHER INFORMATION: n = A, C, G or T
<220> FEATURE:
<221> NAME/KEY: misc_feature
<222> LOCATION: (11)..(11)
<223> OTHER INFORMATION: n = T or C
<220> FEATURE:
<221> NAME/KEY: misc_feature
<222> LOCATION: (12)..(12)
<223> OTHER INFORMATION: n = A or G
<220> FEATURE:
<221> NAME/KEY: misc_feature
<222> LOCATION: (15)..(15)
<223> OTHER INFORMATION: n = A or G
<220> FEATURE:
<221> NAME/KEY: misc_feature
<222> LOCATION: (18)..(18)
<223> OTHER INFORMATION: n = C or T
<220> FEATURE:
<221> NAME/KEY: misc_feature
<222> LOCATION: (21)..(21)
<223> OTHER INFORMATION: n = C or T

<400> SEQUENCE: 7
ttnacnaang nntcntantg ntc                                            23

<210> SEQ ID NO 8
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (3)..(3)
<223> OTHER INFORMATION: n = G or T
<220> FEATURE:
<221> NAME/KEY: misc_feature
<222> LOCATION: (6)..(6)
<223> OTHER INFORMATION: n = A or G
<220> FEATURE:
<221> NAME/KEY: misc_feature
<222> LOCATION: (9)..(9)
<223> OTHER INFORMATION: n = A C, G or T
<220> FEATURE:
<221> NAME/KEY: misc_feature
<222> LOCATION: (11)..(11)
<223> OTHER INFORMATION: n = T or C
<220> FEATURE:
<221> NAME/KEY: misc_feature
<222> LOCATION: (12)..(12)
<223> OTHER INFORMATION: n = A or G
<220> FEATURE:
```

```
<221> NAME/KEY: misc_feature
<222> LOCATION: (15)..(15)
<223> OTHER INFORMATION: n = A or G
<220> FEATURE:
<221> NAME/KEY: misc_feature
<222> LOCATION: (18)..(18)
<223> OTHER INFORMATION: n = C or T
<220> FEATURE:
<221> NAME/KEY: misc_feature
<222> LOCATION: (21)..(21)
<223> OTHER INFORMATION: n = C or T

<400> SEQUENCE: 8
ttnacnaang nntcntantg ntc                                              23

<210> SEQ ID NO 9
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Synthetic sequence

<400> SEQUENCE: 9

Glu Tyr Ile Lys Ala Asn Ser Lys Phe Ile Gly Ile Thr Glu Leu
1               5                   10                  15

<210> SEQ ID NO 10
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Synthetic sequence

<400> SEQUENCE: 10

Leu Ser Glu Ile Lys Gly Val Ile Val His Arg Leu Glu Gly Val
1               5                   10                  15
```

NUCLEIC ACID AND AMINO ACID SEQUENCES, AND VACCINE FOR THE CONTROL OF ECTOPARASITE INFESTATIONS IN FISH

This application is the U.S. National Phase of, and Applicants claim priority from, Internal bearing Serial No. 2007-0124 field May 2007, which are incorporated herein by reference.

FIELD OF THE INVENTION

The present invention relates to aquatic biotechnology, in particular with a gene sequence and the encoded polypeptide, which are protective antigens against ectoparasite infestations in fish, vaccines comprising these antigens and methods for inducing an immune response against ectoparasites in aquatic organisms.

BACKGROUND OF THE INVENTION

Sea lice (Copepoda, Caligidae) are the most widely distributed marine pathogens in salmon industry in the last 30 years. They also spread in the final 15 years to other culture species and wild salmonid populations (Pike, A. W. y Wadsworth, S. L. (2000). Advances in Parasitology 44:233-337, Ragias, V. et al. (2004). Aquaculture 242: 727-733). There are three major genera of sea lice: *Pseudocaligus, Caligus* and *Lepeophtheirus*.

Considering salmonid production throughout northern hemisphere, one of these species, *Lepeophtheirus salmonis*, is the responsible for the main disease outbreaks in salmonid farms. This parasite, just in 2004, was the responsible for direct and indirect losses in worldwide aquaculture, of 100 millions of US dollars (Johnson, S. C., et al. (2004). Zool Studies 43: 8-19). All the sea lice developmental stages in which the parasite is attached to the host, feed on host mucus, skin and blood. The sea lice adhesion and feeding produce lesions that differ in their nature and severity, depending on the sea lice specie, their abundance, the developmental stages present and the host specie (Johnson, S. C et al., "Interactions between sea lice and their hosts". En: Host-Parasite Interactions. Editors: G. Wiegertjes and G. Flik, Garland Science/Bios Science Publications, 2004, pp. 131-160). In the southern hemisphere, *Caligus rogercresseyi* is the most important specie affecting chilean salmon industry (González, L. y Carvajal, J. (2003). Aquaculture 220: 101-117). In the case of severe illness, like the one observed in Atlantic salmon (*Salmo salar*), when the fish are infected by a high number of *L. salmonis*, extensive damaged and hemorrhagic skin areas are observed in the head and fish back. Also, a distinct area of erosion and sub-epidermal hemorrhage in the perianal region can be seen (Grimnes, A. et al. (1996). J Fish Biol 48: 1179-1194). Sea lice can cause host physiological changes including a stress response, reduction of immune functions, osmorregulation failure and death, if the infection is not treated (Johnson, S. C., et al. (2004). Zool Studies 43: 8-19).

A wide range of chemicals had been used to control sea lice infestations like hydrogen peroxide, organophosphates, ivermectin and other related compounds like emamectin benzoate, molting regulators and pyrethrins (MacKinnon, B. M. (1997). World Aquaculture 28: 5-10; Stone J., et al. (1999). J Fish Dis 22: 261-270). The treatments against sea lice can be apply by immersion baths like organophosphates and pyrethroyds or orally, as ivermectin. These immersion baths are difficult to perform. In addition they are expensive and can have significant effects over fish growth after treatments (MacKinnon, B. M. (1997). World Aquaculture 28: 5-10). Besides, the chemicals commonly used by immersion baths are not effective in all sea lice developmental stages. To date, the use of oral treatments such as SLICE® (emamectin benzoate) is predominant in salmon industry. SLICE®, unlike chemicals administered by immersion, give a short protection against re-infection. This treatment, although is easier to apply compared to immersion baths, is also expensive and requires a period of time before the fish can be destined for human consumption (Stone J., et al. (1999). J Fish Dis 22: 261-270).

There are evidences which suggest the development of resistance against conventional treatments in *L salmonis*, particularly in populations frequently treated (Denholm, I. (2002). Pest Manag Sci 58: 528-536). This fact together with the necessity of reducing costs and threats to the environment, make imperative the development of new approaches like vaccines to control sea lice infestations in fish. The experience with terrestrial parasites demonstrated that a successful vaccine needs to be comprised for one or more concealed antigens with low or not homology with the host proteins. Sea lice are ectoparasites that feed on host mucus, skin and blood and then, only have limited contact with the host immune system (Boxaspen, K. (2006). ICES Journal of Marine Science 63: 1304-1316). In these cases, it was observed host immune response suppression due to the production of immunomodulatory proteins by the parasite at the adhesion and feeding site (Wikel, S. K., et al., "Arthropod modulation of host immune responses". En: The Immunology of Host-Ectoparasitic Arthropod Relationships. Editors: Wikel, S. K., CAB Int., 1996, pp. 107-130). These proteins have been investigated for their use as candidate vaccines to control sea lice infestations. They have been patented and have been evaluated in assays performed in vitro to study its effects over the host immune system (Patent No. WO2006010265: RECOMBINANT VACCINES AGAINST CALIGID COPEPODS (SEA LICE) AND ANTIGEN SEQUENCES THEREOF). Tripsins, vitellogenin-like proteins and host adhesion proteins are some of the molecules studied as potential antigens (Johnson, S. C., et al. (2004). Zool Studies 43: 8-19; Boxaspen, K. (2006). ICES Journal of Marine Science 63: 1304-1316).

In general, vaccines are safer than chemical treatments for both, fish and environment. Nevertheless, until now there are not commercial vaccines available against sea lice. Experimental vaccines against *L salmonis*, which employ animal whole extracts, have been developed. These vaccines were not protective since their administration resulted in minor changes in *L salmonis* fecundity (Grayson T. H., et al. (1995). J Fish Biol 47: 85-94).

The identification of targets for sea lice prevention and treatment have not been successful as a result of the poor knowledge about the mechanisms involved in the pathology of sea lice infestations in salmons. This handicap makes difficult the progress of researches related to recombinant vaccines development. The reality is that up to the moment an effective vaccine against these ectoparasites has not been developed.

In other arthropods like ticks, genes involved in different tick's genera reproduction and feeding (Almazán et al. (2003). Vaccine 21:1492-1501) have been identified, employing expression immunization libraries. The results based on RNA interference (de La Fuente et al. (2005). Parasitol Res. 96:137-141) and immunization trials (Almazán et al. (2005). Vaccine 23: 4403-4416) suggest that these genes might be good candidates for vaccine development against different tick species which infest mammals. One of the tick's studied proteins, cement protein, which is produced in the tick salivary glands appear to be a good candidate to confer protection against different tick species (Adama, R. et al. (2005). Vaccine 23: 4329-4341) and consequently, against opportunistic pathogens which use ticks as their hosts (Labuda, M. et al. (2006). PLoS Pathogens 2(4): 251-259).

DESCRIPTION OF THE INVENTION

The current invention solves the problem discussed before, providing new nucleic acid and amino acid sequences as components of a vaccine against ectoparasite infestations in fish. These vaccines comprise an immunogenic amount of a DNA fragment isolated from *Caligus rogercresseyi* adults and/or a polypeptide encoded by this DNA fragment, formulated in a suitable adjuvant.

The new gene which comprises the sequence identified as SEQ ID No. 1, named in this document as my32, was isolated by using degenerate oligonucleotides. These primers were designed based on sequences similar to the 4D8 protein (or subolesin) found in different insects and arachnids: *Drosophila melanogaster* (GeneBank accession number: AAN12062), *D. pseudoobscura* (GeneBank accession number: EAL30734), *Apis mellifera* (GeneBank accession number: XP_395252) and the tick *Ixodes scapularis* (GeneBank accession number: AAV67031). At the DNA level, the isolated fragment only has a short region of homology of 56 nucleotides comprised between nucleotide 476 and nucleotide 532 of the isolated sequence, and nucleotide 321-nucleotide 377 of the 4D8 gene from *Rhipicephalus sanguineus*. In terms of amino acid sequence, the sequence of the new antigen has low homology (<43%) with the sequences mentioned above and other in the GeneBank database.

The isolated nucleic acid encodes for a polypeptide, which amino acid sequence is identified in the present invention as SEQ ID No. 2, and is named hereafter MY32. It is also an object of the present invention an amino acid sequence in which one or more amino acid residues have been removed, substituted or added to the sequence identified as SEQ ID No. 2 and keeps its potential to induce an immune response against ectoparasites in fish.

As the main result, it was found that the new gene and/or the corresponding polypeptide (SEQ ID No. 2) expressed by recombinant DNA technology in the yeast *Pichia pastoris*, produces humoral IgM immune response and important damages in ectoparasite development and reproduction. Moreover, it was observed a significant reduction in the number of parasites per fish in challenge experiments.

The use of this new antigen offers several advantages over the traditional methods employed in salmon industry to treat sea lice infestations described above. The parasite life cycle is interrupted due to the presence of specific antibodies against this protein and the activation of the host cellular immune response. These mechanisms together produce a reduction in the parasite body weight. They also affect the parasite reproduction and consequently, reduce the infestation levels, because of the individual damage which ultimately leads to the reduction of caligid populations. These effects are coupled with both a minimal environmental effect and low risk for human consumption. Besides, as a result of the vaccine administration, the infestation levels of opportunistic pathogens like *Piscirickettsia salmonis*, an intracellular pathogen that causes large losses in salmon culture, were diminished. The effects of the use of this new gene and the encoded protein, are surprising and unexpected, bearing in mind that some authors have considered that host blood is not the main component of the sea lice diet (approximately 15-25% of consumed tissue) and the female does not ingest more blood compared to males as occurs in terrestrial blood-feeding parasites (Bricknell, I. R et al., (2004). Caligus 8: 6; Wagner, G. N. y McKinley, R. S. (2004). J. Fish. Biol. 64:1027-1038). Currently, the knowledge to about the molecular mechanisms involved in sea lice digestion is sparse. Thus, it is not obvious that crustacean's physiology is similar to arachnids (Raynard, R. S. et al. (2002). Pest Management Science 58: 569-575).

In one of the embodiment of the present invention, the compositions which comprise the polypeptide defined by the amino acid sequence identified as SEQ ID No. 2, stimulate the IgM immune response in fish, producing damages in the ectoparasites and reducing sea lice infestations levels.

The polypeptide coding sequence was obtained by Polymerase Chain Reaction (PCR) using complementary DNA (cDNA) from adult *Caligus* spp. as template and degenerate oligonucleotides. Polypeptides which comprise in their polypeptide chain an amino acid sequence at least 50% homologous to the SEQ. ID No. 2, and produce an immune response against ectoparasite infestations in salmonids and other fish species, are also subject of the present invention.

In a particular embodiment of this invention, the nucleotide sequence coding for the polypeptide mentioned before was cloned into a *P. pastoris* expression vector pPS7. This vector has the *P. pastoris* AOX1 promoter (pAOX1), the signal peptide of sucrose invertase 2 (spSUC 2) and the terminator sequence from glyceraldehyde-3-phosphate dehidrogenase, both from *S. cerevisiae*. It also contains a 3'AOX *P. pastoris* chromosomal DNA sequence, necessary for homologous recombination with the yeast genome and the selection marker HIS3 of *S. cerevisiae*. In addition, the vector has a functional replication origin in *Escherichia coli* and the ampicillin resistance gene as bacterial selection marker. The vectors commonly used to generate recombinant yeast strains are generally integrative. Prior to transformation, the plasmids should be linearized to direct homologous recombination by AOX1 region.

The *P. pastoris* MP36 strain was used for extracellular recombinant protein production. This strain is an auxotrophic his3 mutant obtained from *P. pastoris* BKM-90 strain (patent EP0438200), which after transformation with the expression vector acquired a His$^+$ phenotype (Yong V., et al. (1992). HIS-3 gene of *Saccharomyces cerevisiae* complement his$^-$ mutation in yeast *Pichia pastoris*. Biotecnologia Aplicada 9: 55-61).

The present invention also comprises the sequence identified as SEQ ID No. 2, or a fragment, obtained from recombinant or natural sources or by chemical synthesis. To obtain the polypeptide of interest, a bacterial expression system and/or yeast different from *P. pastoris* and/or other systems for recombinant protein production well known in the art can be used.

In another embodiment of the present invention, the target gene was also cloned in pVAX vector (Invitrogen). This vector is specifically designed for use in the development of DNA vaccines. With a minimal sequence this vector provides highest level expression of recombinant proteins while minimizing extraneous genetic elements. The pVAX vector meets the U.S. Food and Drug Administration (FDA) guidelines for DNA vaccine design.

This invention comprises as well a vaccine composition against ectoparasites that affect salmonids and other species, which contains the polypeptide, identified as SEQ ID No. 2 or a polypeptide at least 50% homologous with SEQ. ID No. 2. As part of this invention, two or more promiscuous T cell epitopes were incorporated to the polypeptide identified as SEQ ID No. 2. Several studies have established the potential of promiscuous T cell epitopes incorporated as fusion proteins in chimeric peptides and proteins to increase its immunogenicity (El Kasmi K C. et al. (2000). J Gen Virol 81:729-35). These epitopes can be derived from natural immunogens of viral or bacterial origin. These natural epitopes can also be modified by addition, deletion or substitution of one or multiple amino acids to obtain a vaccine candidate that can be tested by its ability to increase the response to a specific antigen. The potential of employing these epitopes in fish vaccines has been demonstrated (Kuzyk M A. et al. (2001) Vaccine 19: 2337-2344).

The effect of this polypeptide over the humoral immune response and sea lice infestation index was evaluated in experiments where the purified polypeptide adjuvated in oil adjuvant was administered to fish by injection. The polypeptide was also effective when it was administered in the feed or by immersion bath. Humoral IgM immune response was increased in vaccinated animals. Challenge experiments demonstrated that the number of parasites per fish were lower in vaccinated fish. Another aspect of the present invention is a vaccine composition against ectoparasitic infestations in salmonids and other fish species which comprises a nucleotide sequence containing the sequence identified as SEQ ID No. 1.

As part of this invention, a method to prevent and treat fish infestations by different ectoparasite species was provided. This method is based on the administration of the polypeptide identified as SEQ ID No. 2, or a polypeptide with an amino acid sequence at least 50% homologous to the SEQ ID No. 2, in a vaccine composition to induce an immune response in aquatic organisms against different ectoparasites species and/or diminished the damage associated with pathogens and opportunistic diseases associated with these infestations.

The polypeptide identified as SEQ ID No. 2 was obtained as a fusion protein with one or two T cell epitopes. These polypeptides, purified and formulated in oil adjuvant, were administered to fish by injection. The success of vaccination was measured in a challenge experiment as the reduction of the number of parasites per fish, compared to the group injected with the polypeptide identified as SEQ ID No. 2 and the group injected with PBS.

In a materialization of the present invention, the composition which comprises the polypeptide MY32 is administered by injection, in doses ranging from 0.1 to 10 µg/g of vaccinated fish body weight. In another aspect of the invention, the vaccine composition is administered in feed formulations, in doses ranging 0.1-300 µg/g of feed, or by immersion baths, in doses between 0.01-1 mg/L of water.

This invention also includes the use of the nucleotide sequence identified as SEQ ID No. 1 alone or in combination with the encoded polypeptide, to make a vaccine composition which comprises naked DNA, to induce an immune response in aquatic organisms against different ectoparasite species, and/or diminished the damages related with these pathogens and opportunistic diseases associated with these infestations. A naked DNA vaccine containing the cDNA from *Caligus* spp. and a combination of the purified polypeptide/naked DNA were evaluated. Good results, in terms of IgM immune response and reduction of the number of parasites per fish, were obtained.

EXAMPLES

Example 1

Figure 1:
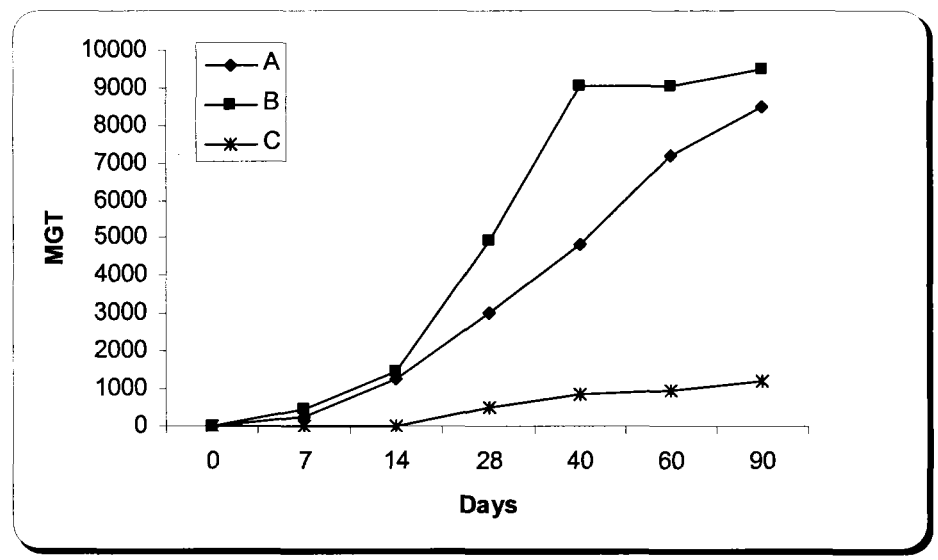
FIG. 1. Humoral immune response obtained with different doses of the protein named MY32, administered by intraperitoneal injection to 35 g fish (*Salmo salar*). The graphic shows the geometric mean of the antibody titers (GMT) versus time. The experimental groups are: A. Purified recombinant MY32 protein: 0.5 µg/g of body weight); B. Purified recombinant MY32 protein: 1 µg/g of body weight; Negative control: Phosphate Buffered Saline (PBS) adjuvated in oil adjuvant.

Isolation and Cloning of the my32 Gene

The coding sequence for the MY32 polypeptide was obtained by PCR from cDNA of *Caligus rogercresseyi*, using degenerate oligonucleotides designed from previously reported sequences for suboleosin in different arthropods.

The oligonucleotides were:

```
Oligonucleotide that hybridyze with 5' fragment:
                                         SEQ ID NO: 3
ATG GC(T/C) TG(T/C) GC(T/C/G/A) AC(T/C/A/G)
(T/C)T(T/C) AA(A/G)

SEQ ID NO: 4
ATG GC(T/C) TG(T/C) GC(T/C/G/A) AC(T/C/A/G)
(T/C)T(A/G) AA(A/G)

SEQ ID NO: 5
ATG GC(G/A) TG(T/C) GC(T/C/G/A) AC(T/C/A/G)
(T/C)T(T/C) AA(A/G)

SEQ ID NO: 6
ATG GC(G/A) TG(T/C) GC(T/C/G/A) AC(T/C/A/G)
(T/C)T(A/G) AA(A/G)

Oligonucleotide that hybridyze with 3' fragment:
                                         SEQ ID NO: 7
TT(A/C)AC(A/G)AA(A/C/G/T)G(T/C) (A/G)TC(A/G)TA
(C/T)TG(C/T)TC
```

-continued

SEQ ID NO: 8
TT(G/T)AC(A/G)AA(A/C/G/T)G(T/C)(A/G)TC(A/G)TA(C/T)TG(C/T)TC

The amplified DNA was cloned into a comercial pGEM Teasy vector (Promega) and it was sequenced with Thermo Sequenase Premixed cycle Sequencer Kit (Amersham Pharmacia) according to manufacturer's instructions.

Example 2

Construction of *Pichia pastoris* Expression Vector Containing the Coding Sequence for MY32 Polypeptide, Transformation of MP36 Strain and Protein Expression The my32 gene was amplified by PCR with specific oligonucleotides. These specific oligonucleotides incorporated a histidine tail to facilitate the protein immunodetection and purification. The PCR product was treated with T4 polynucleotide kinase enzyme to phosphorylate the gene ends and facilitate its cloning into the expression vector. The expression vector pPS7 was enzymatically digested with Nco I restriction endonuclease, treated with nuclease S1 and phosphatase alkaline to blunt and desphosphorylate the ends. The recombinant plasmid obtained was named pPS7-my32.

Prior to transformation, the plasmids were linearized with Pvu II restriction enzyme. The *P. pastoris* strain MP36 was transformed by electroporation with the recombinant expression vector. This strain is an auxotrophic his3 mutant which acquired the His$^+$ phenotype after transformation.

The transformants identified by Dot Blot were analyzed by Southern Blot to determinate in which the integration event occurs. The gene my32 is under the regulation of AOX1 promoter. This promoter is inducible by methanol. The protein was obtained at high levels in the periplasm. It was solubilized and purified by affinity chromatography to metal ions employing Ni-NTA (Quiagen) and obtained 95% pure.

Example 3

Construction of my32 DNA Expression Vector in Eukaryotic Cells for Naked DNA Vaccine The gene my32 was excised from pGEM T easy (Promega) by digestion with EcoR I. The insert was purified by QiaQuick kit (Qiagen, Hamburg, Germany) and ligated to pVAX vector (Invitrogen) previously digested with EcoR I. Recombinant DNA employed in immunization experiments was purified by Endo Free Plasmid Mega kit (Qiagen, Hamburg, Germany).

Example 4

Humoral Immune Response to Different Doses of Purified Recombinant Protein MY32 Administered by Intraperitoneal Injection Three experimental groups of Atlantic salmon (*Salmo salar*) of 35 g mean weight were intraperitoneally injected with the purified polypeptide in oil adjuvant. The experimental groups (of 50 animals each) were:
  A. Purified recombinant MY32 protein: 0.5 µg of body weight.
  B. Purified recombinant MY32 protein: 1 µg/g of body weight.
  C. Negative control: PBS in oil adjuvant.

The dynamic of the IgM humoral immune response was measured by ELISA in a 90 days period. High IgM titers were demonstrated in the two doses assayed (FIG. 1).

Example 5

Challenge Experiment: Artificial *Caligus rogercresseyi* Infestations in *Salmo salar* Previously Immunized by Intraperitoneal Injection Two hundred salmon of 35 g of average body weight were distributed into two experimental groups, 100 fish per group. Salmons from one group were injected with the purified protein at the dose of 1 µg/g of body weight adjuvated in oil adjuvant Montanide 888 at week 0. Negative control group received a PBS injection adjuvated in Montanide 888.

Two weeks later, salmon were extensively infested with an average of 100 parasites per fish, at copepodid developmental stage. At day 60, the number of parasites per fish was counted, finding a reduction in more than 80% (Table 1) in the group injected with the purified polypeptide, as compared to negative control group. Fish sera were collected at weeks 0, 4 and 8 and they were evaluated by ELISA for MY32 IgM specific response. High antibody titers were found at weeks 4 and 8 (Data not shown).

TABLE 1

Effect of the intraperitoneal injection with purified MY32 protein on the number of parasites per fish at days 28 and 60 after the injection.

| Experimental groups | Number of parasites/fish | |
|---|---|---|
| | 28 days | 60 days |
| Purified MY32 protein adjuvated in oil adjuvant (1 µg/g of body weight) | 45 ± 5 | 15 ± 3 |
| Negative control: PBS in oil adjuvant | 92 ± 7 | 90 ± 8 |

Example 6

Figure 2:
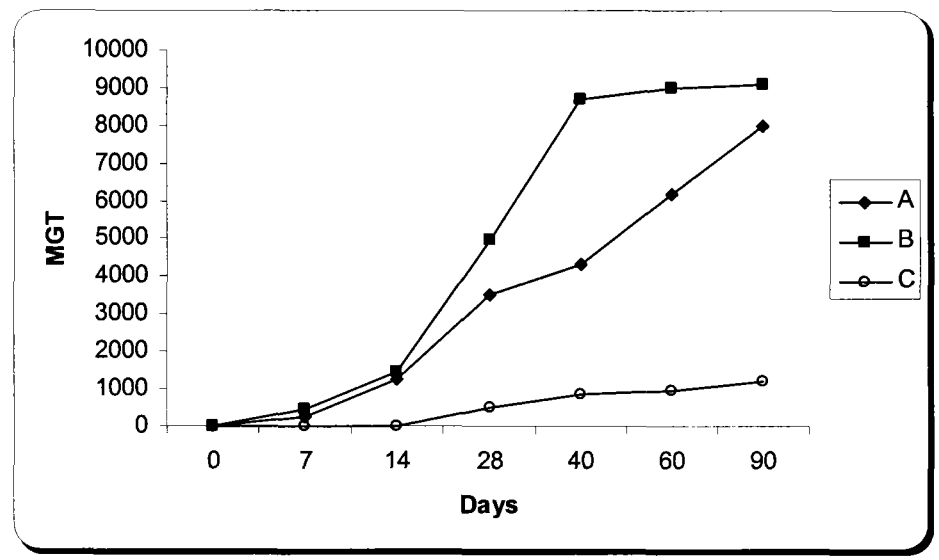
FIG. 2. Humoral immune response obtained with different doses of the protein named MY32, orally administered to 35 g salmons. The graphic shows the geometric mean of the antibody titers (GMT) versus time. The experimental groups are: A. Purified recombinant MY32 protein: 0.5 µg/g of feed; B. Purified recombinant MY32 protein: 1 µg/g of feed; Negative control: Salmonid standard feed without MY32.

Humoral Immune Response in Fish Vaccinated with Different Doses of Purified MY32, Administered by the Oral Route Three groups of juvenile Atlantic salmon (*Salmo salar*), mean body weight of 35 g, were handled. An oral formulation was prepared including the MY32 polypeptide in the salmon basal diet. Fishes belonging to negative control group were fed with basal diet alone. The fishes were fed once a day for five days. The experimental groups (of 50 fishes each) were:
  A. Feed containing purified MY32 protein at the dose of 0.5 µg/g of feed
  B. Feed containing purified MY32 protein at the dose of 1 µg/g of feed
  C. Negative control: Commercial feed By using ELISA, the time course of the IgM humoral immune response was evaluated in a 90 days period, which showed high antibody titers at the doses assayed (FIG. 2).

Example 7

Challenge Experiment in *Salmo salar* Previously Immunized with the Purified Polypeptide MY32 and Infested with *Lepeophtheirus salmonis*

Figure 3:
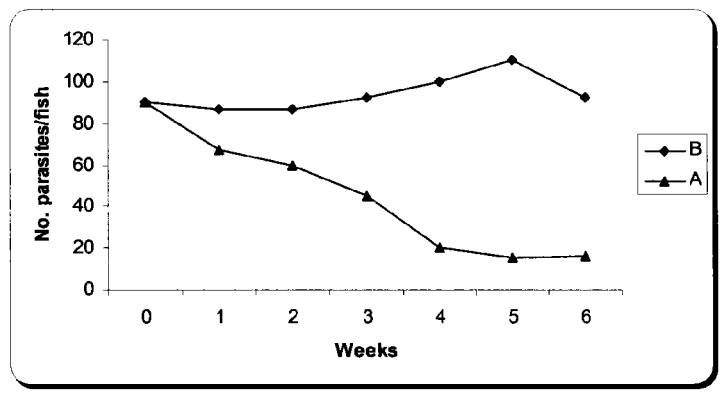
FIG. 3. Challenge experiment in *Salmo salar* immunized with the purified polypeptide MY32, administered at the dose of 1 µg/g of feed. Fish were infested with *Lepeophtheirus salmonis*. The experimental groups are: A. Feed containing MY32 protein at the dose of 1 µg/g of feed; B. Negative control: Salmonid standard feed without MY32.

Two hundred salmons with an average body weight of 35 g were distributed into two groups of 100 fishes each one. An oral formulation was prepared mixing the purified MY32 polypeptide with salmon basal diet, at the dose of 1 μg/g of body weight. Negative control group was fed of basal diet alone. Fishes were fed once a day for 5 days with:
- A. Feed containing purified MY32 protein at the dose of 0.5 μg/g of feed
- B. Feed containing purified MY32 protein at the dose of 1 μg/g of feed
- C. Negative control: Commercial feed Afterwards, fishes were infested with an average of 90-95 sea lice per fish, approximately. The parasites were counted weekly for 6 weeks. It was observed a reduction in a number of parasites per fish in oral vaccinated groups as compared to negative control group (FIG. 3). At weeks 4 and 8, sera were collected and evaluated by ELISA for IgM against MY32. High antibody titers were found.

Example 8

Salmon Immunization with Naked DNA of the Sequence Coding for my32 Gene and Evaluation of Infestation by *Caligus rogercresseyi*

Figure 4:
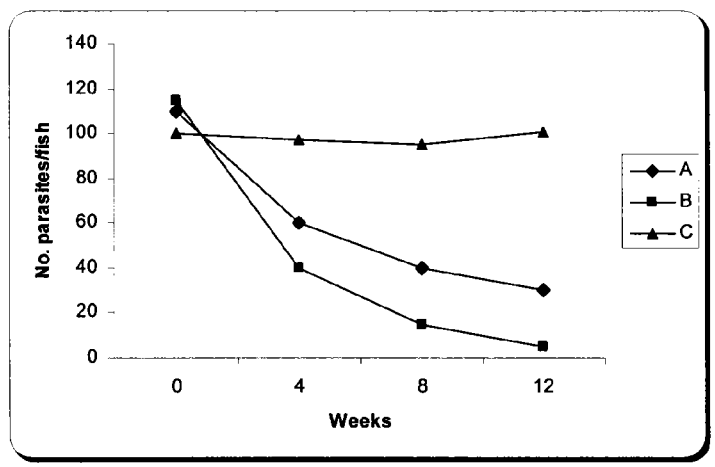
FIG. 4. Effect on the number of parasites per fish of the salmon immunization with the DNA coding for the polypeptide MY32 or the combination DNA/purified protein. The fish were immunized by intramuscular injection containing 25 µg of plasmid DNA having the my32 gene from *C. rogercresseyi* (group A) or with 25 µg of plasmid DNA having the my32 gene from *C. rogercresseyi* plus the purified polypeptide at a concentration of 0.5 µg/g of body weight (group B). Control fish were immunized with the backbone expression vector (group C).

Hundred fifty salmons (*Salmo coho*) of 35 g in average weight were distributed into three groups of 50 fishes each one. Fishes were immunized with an intramuscular injection of 25 μg of the plasmid DNA containing the gene my32 from *C. rogercresseyi* (group A) or 25 μg of the plasmid DNA containing the gene my32 combined with the encoded polypeptide at a concentration of 0.5 μg/g of body weight (group B). Negative control fishes were immunized with the plasmid backbone vector (group C). Fishes from groups A and B showed higher IgM titer as compared to the negative control group, at weeks 4 and 7 post vaccination. After 4 weeks, fishes infested with an average of 100 sea lice per fish were incorporated to the tanks. The experiment was followed by counting the number of parasites for 12 weeks. The results showed that groups A and B had lower number of parasites as compared to group C. The reduction in the infestation levels was 70% for group A (naked DNA) and 95% for group B (naked DNA+polypeptide) as compare to negative control group (FIG. 4).

Example 9

Challenge Experiment in Salmons *Salmo salar* Previously Immunized by Immersion Bath and Infested with *C. rogercresseyi*

Figure 5:
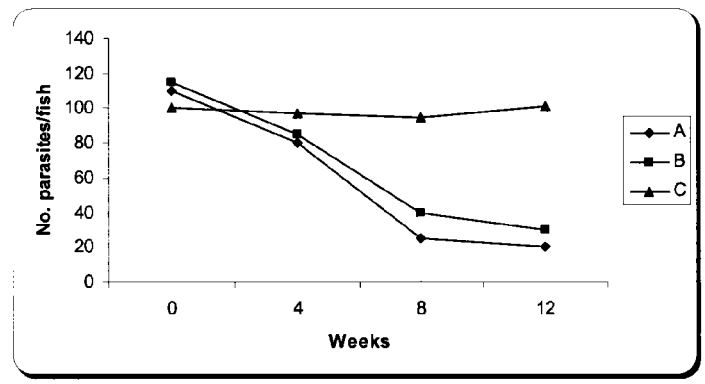
FIG. 5. Challenge experiment in *Salmo salar*, previously immunized by immersion bath and infested with *C. rogercresseyi*. The graphic shows the average number of parasite per fish versus time. The experimental groups are: A: Group immunized with the plasmid containing my32 gene at the dose of 0.01 mg/L of water; B: MY32 polypeptide at the dose of 0.1 mg/L of water; C: Negative control.

Hundred fifty salmons of 30 g as average weight were distributed into three groups of 50 fishes each one. For immersion bath, the water level in the tanks was decreased. The plasmid pVAXmy32 was administered to one group. Another group received the purified protein and a control group received PBS. The immersion bath treatment was done for 90 min. The experimental groups were:
A: Plasmid pVAXmy32 at the dose of 0.01 mg/L of water.
B: Purified MY32 protein at the dose of 0.1 mg/L of water
C: Negative control group: PBS After three weeks post vaccination, salmon were extensively infested with an average of 90-95 sea lice (*C. rogercresseyi*) per fish, approximately. The experiment was conducted for 12 weeks and showed that fishes immunized with my32 gene or MY32 polypeptide had a lower number of parasites, as compared to negative control group (FIG. 5).

Example 10

Challenge Experiment, with Infestation by *Caligus rogercresseyi* of *Salmo salar* Previously Immunized by Intraperitoneal Injection with Purified MY32 Polypeptide and the MY32-Promiscuous T Cell Epitopes Fusion Proteins Five hundred salmons of 35 g of weight were distributed into 5 groups of 100 fishes per group. Fishes were intraperitoneally injected at week 0. The experimental groups were:
Group 1: MY32 protein adjuvated in Montanide 888, at the dose of 1 μg/g of body weight. Group 2: Purified MY32-tetanus toxoid ttP2 promiscuous T cell epitope (830-844 QYIKANSKFIGITEL; (SEQ ID NO; 9)GenBank X04436) protein adjuvated in oil adjuvant is Montanide 888 (1 μg/g of body weight). Group 3: Purified MY32measles virus promiscuous T cell epitope (288-302 LSEIKGVIVHRLEGV; GenBank M81903) protein adjuvated in oil adjuvant Montanide 888 (1 μg/g of body weight). Group 4: Purified MY32-ttP2-measles virus promiscuous T cell epitopes protein adjuvated in oil adjuvant Montanide 888 (1 μg of body weight). Group 5: Negative control group was injected with PBS in oil adjuvant.

Two weeks later, the fishes were infested with an average of 100 sea lice per fish at copepodid stage. On day 60, it was found a reduction of the number of parasites per fish in more than 95% (Table 2) in the group injected with the purified MY32-ttP2-measles virus promiscuous T cell epitopes as compared to negative control group. Sera from the animals were collected at weeks 0, 4 and 8 and evaluated for IgM against MY32 by ELISA. High antibody titers were found at weeks 4 and 8 (data not shown) in all the groups immunized with the protein or the protein fused to promiscuous T cell epitopes. The highest titer was found in the group vaccinated with MY32-ttP2-measles virus promiscuous T cell epitopes.

TABLE 2

Effect of the intraperitoneal injection of purified MY32 protein and the fusion protein MY32-promiscuous T cell epitopes, over the number of parasites per fish, at days 28 and 60 after injection.

| Experimental group | Average number of parasites per fish | |
|---|---|---|
| | Day 28 | Day 60 |
| Group 1 | 50 ± 5 | 20 ± 3 |
| Group 2 | 30 ± 3 | 8 ± 2 |
| Group 3 | 32 ± 6 | 9 ± 3 |
| Group 4 | 15 ± 2 | 3 ± 1 |
| Group 5 | 92 ± 7 | 90 ± 8 |

INCORPORATION OF SUBSTITUTE SEQUENCE LISTING

Incorporated herein by reference in its entirety is the Sequence Listing for the application. The Sequence Listing is disclosed on a computer-readable ASCII text file title, "sequence listing 12414.txt", created on Jan. 24, 2014. The sequence listing. txt file is 7.84 kb in sixe.

The invention claimed is:

1. An isolated nucleic acid sequence comprising the cDNA sequence identified as SEQ ID NO: 1.

2. An immunogenic composition comprising the polypeptide identified as SEQ ID NO: 2 formulated in a suitable adjuvant.

3. An immunogenic composition according to claim 2, wherein the polypeptide is obtained by recombinant way or chemical synthesis.

4. An immunogenic composition comprising an isolated nucleic acid sequence comprising the cDNA nucleotide sequence identified as SEQ ID NO: 1.

5. A method for inducing an immune response in a salmonid against sea lice, and/or reducing number of sea lice in the salmonid, said method comprising administering an effective amount of a composition comprising the polypeptide identified as SEQ ID NO: 2 to the salmonid.

6. The method according the claim 5, wherein the composition is administered by injection at doses ranging between 0.1-10 µg/g of body weight of the salmonid.

7. The method according the claim 5, wherein the composition is administered in feed formulations at doses ranging between 0.1-300 µg/g of feed.

8. The method according the claim 5, wherein the composition is administered by immersion baths at doses ranging between 0.01-1 mg/L of water.

9. A method for inducing an immune response in a salmonid against sea lice, and/or reduce the number of sea lice in the salmonid, said method comprising administering an effective amount of a composition comprising an isolated nucleic acid sequence comprising SEQ ID NO: 1 to the salmonid.

10. A fusion polypeptide comprising: 1) an isolated polypeptide consisting of the amino acid sequence identified as SEQ ID NO: 2 and 2) a peptide consisting of a promiscuous T cell epitope of viral or bacterial origin.

11. The fusion polypeptide of claim 10 wherein the promiscuous T cell epitope is SEQ ID NO: 9 or SEQ ID NO: 10 or combination thereof.

12. A vector comprising the isolated nucleic acid sequence according to claim 1.

13. A vector comprising an isolated nucleic acid sequence coding for a polypeptide which comprises an amino acid sequence identified as SEQ ID NO: 2.

* * * * *

UNITED STATES PATENT AND TRADEMARK OFFICE
CERTIFICATE OF CORRECTION

| | | |
|---|---|---|
| PATENT NO. | : 9,034,338 B2 | Page 1 of 1 |
| APPLICATION NO. | : 12/601974 | |
| DATED | : May 19, 2015 | |
| INVENTOR(S) | : Carpio Gonzalez et al. | |

It is certified that error appears in the above-identified patent and that said Letters Patent is hereby corrected as shown below:

In the specification,

Column 4, line 5

Now reads: "knowledge to about the"
Should read: -- knowledge about the --

Column 10, line 67

Now reads: "txt file is 7.84 kb in sixe."
Should read: -- txt file is 7.84 kb in size. --

Signed and Sealed this
Twenty-second Day of December, 2015

Michelle K. Lee
*Director of the United States Patent and Trademark Office*